United States Patent [19]

Niimura et al.

[11] Patent Number: 5,416,012
[45] Date of Patent: May 16, 1995

[54] PROCESS FOR PRODUCING NADH OXIDASE

[75] Inventors: Youichi Niimura; Michio Kozaki, both of Tokyo; Hisashi Yamagata, Toride; Miki Ikuta, Tsuchiura; Yasurou Kurusu; Hideaki Yukawa; Makiko Kukushima; Masato Terasawa, all of Ibaraki, all of Japan

[73] Assignee: Mitsubishi Petrochemical Co., Ltd., Tokyo, Japan

[21] Appl. No.: 242,004

[22] Filed: May 12, 1994

Related U.S. Application Data

[60] Division of Ser. No. 975,163, Nov. 12, 1992, Pat. No. 5,336,608, which is a continuation of Ser. No. 483,814, Feb. 23, 1990, abandoned.

[30] Foreign Application Priority Data

Feb. 28, 1989 [JP] Japan .................................. 1-45445
Aug. 16, 1989 [JP] Japan .................................. 1-211167

[51] Int. Cl.6 ........................ C12N 9/02; C12N 15/70; C12N 15/53
[52] U.S. Cl. ............................... 435/189; 435/252.33; 435/320.1
[58] Field of Search .................. 435/189, 720.1, 252.33

[56] References Cited

U.S. PATENT DOCUMENTS 4,954,445 9/1990 Yoshihama et al. ................ 435/191

FOREIGN PATENT DOCUMENTS 0295622 12/1988 European Pat. Off. .
3725851 2/1988 Germany .
3251082 10/1988 Japan .................................. 435/189
8400383 2/1984 WIPO .

OTHER PUBLICATIONS

Niimura et al., "A New Facultative Anaerobic Xylan-using Alkalophite Lacking Cytochrome, Quinone, and Catalase", Agric. Biol. Chem. vol. 51, No. 8, pp. 2271-2775 (1987).
Koike et al., "Purification and Characterization of NADH Oxidase From A Strain of Leuconostoc mesenteroides", J. Biochem. vol. 97, pp. 1279-1288 (1985).
Reinards et al. (1981) Eu. J. Biochem. 120, pp. 329-337.
Young et al. (1983) Proced. Natl. Acad. Sci. 80, pp. 1194-1198.
Sugimori et al., Chemical Abstracts, vol. 111, No. 13, 25 Sep. 1989, p. 543, Abstract No. 113780h.
Hitachi, Ltd., Chemical Abstracts, vol. 103, No. 11, 16 Sep. 1985, p. 501, Abstract No. 86511x.
Nagata, Chemical Abstracts, vol. 109, No. 13, 26 Sep. 1988, p. 351, Abstract No. 107532w.
Burstein et al., Chemical Abstracts, vol. 96, No. 15, 12 Apr. 1982, p. 291, Abstract No. 118156r.
Niimura et al., FEMS Microbiology Letters, vol. 61, 1989, pp. 79-84.

*Primary Examiner*—Charles L. Patterson, Jr.
*Attorney, Agent, or Firm*—Wenderoth, Lind & Ponack

[57] ABSTRACT

A process for producing an NADH oxidase which comprises culturing alkalophilic, facultative anaerobic NADH oxidase-producing bacteria having the optimum growth pH in an alkaline region in medium and collecting said NADH oxidase from the culture; and a plasmid used for the said process.

30 Claims, 2 Drawing Sheets

PROCESS FOR PRODUCING NADH OXIDASE

This is a divisional application of Ser. No. 07/975,163 filed Nov. 12, 1992, now U.S. Pat. No. 5,836,608, which is a continuation application of now abandoned Ser. No. 07/483,814 filed Feb. 23, 1990.

BACKGROUND OF THE INVENTION

The present invention relates to a process for microbiologically producing reduced nicotinamide adenine dinucleotide (hereafter simply referred to as NADH) oxidase which participates in the enzyme reaction which oxidizes NADH to form hydrogen peroxide or water. More specifically, the present invention relates to a process for efficiently producing NADH oxidase having excellent temperature stability by genetic engineering and a plasmid used for the process as well as a transformed microorganism.

Nicotinamide adenine dinucleotide (hereafter simply referred to as $NAD^+$) is a coenzyme of various dehydrogenases and receives hydride ions from the corresponding substrate by the action of dehydrogenase, that is, oxidizes the corresponding substrate and $NAD^+$ itself is reduced to NADH. The formed NADH undergoes oxidation by the action of NADH oxidase, using water or molecular oxygen as a hydrogen receptor, whereby $NAD^+$ is produced.

By allowing the dehydrogenase and NADH oxidase to co-exist, the regeneration system of $NAD^+$ is formed and dehydrogenase reaction of industrially useful optically active compounds or reaction intermediates can be carried out by adding a trace amount of $NAD^+$.

Dehydrogenation involving $NAD^+$ as a coenzyme is generally a reversible reaction and the reaction is largely shifted toward the direction of NADH→$NAD^+$ at neutral pH. In such a case, it is difficult to regenerate $NAD^+$ in the dehydrogenase and NADH oxidase system and smoothly progress dehydrogenase reaction of the corresponding substrate. On the other hand, the dehydrogenase reaction is shifted toward the direction of $NAD^+$→NADH in an alkaline region, which regeneration of $NAD^+$ is performed in coupling with NADH oxidase, whereby dehydrogeneration of the corresponding substrate readily proceeds.

As described above, in the case that dehydrogenase reaction is carried out in an industrial scale in the co-presence of dehydrogenase and NADH oxidase using $NAD^+$ as coenzyme, it is important to develop NADH oxidase having a high activity even in an alkaline region and having a wide pH range of its action.

As NADH oxidases which oxidize NADH using molecular oxygen as an electron acceptor, there are hitherto reported oxidases derived from *Lactobacillus plantarum* (Agricultural and Biological Chemistry, 25, 876, 1961), derived from *Streptococcus faecalis* (Journal of Biological Chemistry, 237, 2647, 1962), derived from *Acholeplasma laidlawii* (European Journal of Biochemistry, 120, 329, 1981), derived from *Bacillus megaterium* (Journal of Biochemistry, 98, 1433, 1985), derived from *Leuconostoc mesenteroides* (Journal of Biochemistry, 97, 1279, 1985), etc.

However, NADH oxidases known in these techniques involve disadvantages that the microorganisms are cultured only with difficulty to make mass production difficult (*Acholeplasma laidlawii*, etc.); the enzyme is present in intracellular fraction so that it is difficult to harvest the enzyme and improve its content in the cells (*Bacillus megaterium*, etc.); the enzyme has poor heat stability so that it is difficult to expect that the enzyme could maintain its activity over a long period of time (*Leuconostoc mesenteroides*, etc.). Therefore, these enzymes are not suited or utilized for production in an industrial scale.

SUMMARY OF THE INVENTION

As a result of extensive investigations on NADH oxidase-producing microorganisms suited and utilizable for production in an industrial scale, the present inventors have found that certain anaerobic bacteria having the optimum growth pH in an alkaline region which can survive both in the presence or absence of oxygen (hereafter this microorganism is sometimes referred to as "alkalophilic, facultative anaerobic NADH oxidase-producing bacteria") can produce an NADH oxidase having excellent stability to temperature.

The present inventors have also found that the NADH oxidase can be produced more efficiently by extracting a DNA region containing a gene encoding biosynthesis of the NADH oxidase from the chromosome of the alkalophilic, facultative anaerobic NADH oxidase-producing bacteria, ligating the DNA region with a plasmid vector bearing a DNA region containing a gene encoding autonomous replication of Col E1 type plasmid and culturing a microorganism transformed with the plasmid, for example, *Escherichia coli* K-12 strain, in a growth medium.

The present inventors have further found that this NADH oxidase has a high activity even in an alkaline region and can be used for efficient production of various useful substances including pyruvic acid and can also be used as a reagent of various biochemical reactions, through a coupling reaction with a dehydrogenase.

Thus, according to one aspect of the present invention, there is provided a process for producing NADH oxidase which comprises culturing facultative anaerobic NADH oxidase-producing bacteria having the optimum growth pH in an alkaline region anaerobically or aerobically in medium and collecting the NADH oxidase from the cultured cells.

According to the present invention, in a preferred embodiment of the process described above, there is provided a process for producing NADH oxidase which comprises culturing *Escherichia coli* K-12 microorganism transformed with the plasmid consisting of at least a DNA region containing a gene encoding biosynthesis of the NADH oxidase derived from facultative anaerobic NADH oxidase-producing bacteria having the optimum growth pH in an alkaline region or an NADH oxidase structural gene therein a medium and collecting the NADH oxidase from the cultured cells.

According to another aspect of the present invention, there is provided a plasmid consisting of at least a DNA region containing a gene encoding biosynthesis of an NADH oxidase or an NADH oxidase structural gene derived from facultative anaerobic NADH oxidase-producing bacteria having the optimum growth pH in an alkaline region therein.

According to further aspect of the present invention, there is provided a method for dehydrogenation of substrate in the co-presence of a dehydrogenase and an NADH oxidase using $NAD^+$ as a coenzyme, characterized in that the culture of facultative anaerobic NADH oxidase-producing bacteria having the optimum growth pH in an alkaline region or the treated product thereof containing NADH oxidase-producing bacteria, a plasmid consisting of a gene obtained from the microorganism, a microorganism transformed with the plasmid, a process for producing the NADH oxidase from the microorganism and alkalophilic, facultative anaerobic NADH oxidase-producing bacteria, and dehydrogenase reaction using thus produced NADH oxidase by the process are described in detail.

As the NADH oxidase-producing bacteria which can be used in the present invention, there may be used strains belonging to alkalophilic, facultative anaerobic bacteria and capable of producing NADH oxidase, or variants thereof. A specific example of the strains having these properties which is preferably used in the present invention includes strain Ep01 described in Agricultural and Biological Chemistry, 51, 2271–2275 (1987). This strain is accumulated in and isolated from compost, pH of which is adjusted to an alkaline region. According to the literature, the strain has the following bacteriological properties.

(1) Morphology
  (a) Shape and size of cell: rod, $(0.3–0.6) \times (1.5–2.5)$ μm
  (b) Pleomorphism: negative
  (c) Motility: nonmotile
  (d) Spore: It has heat-resistant endospores.
  (e) Gram staining: positive in the very early stages of growth
  (f) Acid-fast: negative
(2) Growth in various media
  (a) Bouillon-agar medium: It does not grow.
  (b) Gelatin: no liquefaction
(3) Physiological properties
  (a) Growth conditions: It does not grow at pH of 7.0. The optimum pH is between 8.0 and 10.0. The optimum temperature is at about 40° C.
  (b) Oxidase: negative
  (c) Catalase: negative
  (d) Fermentable sugars: D-xylose, D-arabinose, D-ribose, D-glucose, D-mannose, D-fructose, amygdalin, aesculin, salicin, maltose, saccharose, cellobiose, trehalose, soluble starch, pectin and xylan
  (e) It grows in the presence of 3% sodium chloride.
(4) Other properties
  (a) Cell wall component: It contains mesodiaminopimelic acid.
  (b) Cytochrome C: It does not contain cytochrome a, b, c or d.
  (c) Quinone: It contains neither menaquinone nor ubiquinone.
  (d) Guanine and Cytosine are contained in DNA. (GC content) 35.9%
  (e) Cellular fatty acids:
    anteiso acid 23.7%
    iso-branched acid 35.4%
    straight chain acid 37.2%
  (f) It produces xylanase during anaerobic and aerobic culture.

The foregoing properties were surveyed in Bergey's Manual of Systematic Bacteriology, 2 (1986). As the result, the strain shared certain characteristics with many alkalophilic bacteria belonging to the genus Bacillus, gram-negative rods, spore-forming, growth in aerobic culture, growth on a wide variety of carbohydrates, etc. However, unlike xylanase, the strain did not have catalase, was not motile, could not grow on bouillon-agar medium, etc. Furthermore, the strain had no cytochromes and no quinones, showing that the strain is not attributable to the genus Bacillus. The strain was not identical with the genus Clostridium in the constituents of the cellular fatty acids, growth in aerobic culture, etc. There is thus a possibility that the strain does not belong to these known genera. Accordingly, this strain is referred to as unidentified strain Ep01 throughout the specification. The strain has been deposited in the Fermentation Research Institute, Agency of Industrial Science and Technology, 1–3, Higashi 1-chome, Tsukuba-shi, Ibaraki-ken 305, Japan under the deposit number, FERM P-10096 [transferred to international deposit (FERM BP-2744) on Jan. 29, 1990 under the Budapest Treaty].

On the other hand, as nitrogen sources which are nutrient sources of the medium usable for culturing the cells of the aforesaid microorganism, inorganic nitrogen compounds such as ammonia, ammonium sulfate, ammonium chloride, ammonium nitrate, etc. can be used singly or as a mixture. As inorganic metal salts, there may be used, for example, potassium primary phosphate, potassium secondary phosphate, potassium chloride, magnesium sulfate, manganese sulfate, ferrous sulfate, etc. In addition to the inorganic nutrient sources described above, naturally occurring nutrient sources such as corn steep liquor, yeast extract, peptone, etc. may also be supplemented. Furthermore, as carbon sources, there may be supplemented to the medium, for example, glucose, xylose, mannose, fructose, aldose, sucrose, cellobiose, xylan, etc.

In case that the aforesaid NADH oxidase-producing bacteria are cultured in a medium having the composition as described above, it is generally desired that the culture temperature be in a range of from about 20° to about 50° C., preferably about 35° to 45° C. The pH range during the culture is not strictly limited so long as the pH is in an alkaline region of greater than about 7.5. However, it is generally advantageous that the pH range be in a range of from 8 to 10.5, preferably 8.5 to 10.0. It is advantageous to adjust the pH during the culture within the optimum range by adding an alkali such as sodium hydroxide, potassium hydroxide, ammonia, sodium carbonate, etc. A time period for the culture is generally between about 3 and about 24 hours, preferably between 5 and 20 hours. The culture can be performed under aerobic conditions such as aerial agitation, shaking, etc. Alternatively, the culture may also be carried out under oxygen-free anaerobic conditions.

In the case of performing the culture under anaerobic conditions, any condition is applicable and chosen from conventional means used for culturing facultative anaerobic bacteria, for example, oxygen-free gaseous atmosphere such as nitrogen gas, helium gas, argon gas or a gaseous mixture thereof from which oxygen is removed through a reduced copper column, addition of a reducing agent such as titanium (III) citrate, dithionite, etc. thereby to decrease oxidation-reduction potential of the medium and render growth of anaerobic bacteria easy, etc. [cf. "BISEIBUTSU-NO-BUNRIHO", R & D Planning (published in 1986), pages 246 to 274], so long as the condition is effective in the alkaline region which is the optimum for the growth of this strain and does not adversely affect the growth of this strain.

Furthermore, the culture up to the stage where the cells are harvested may not always be performed under anaerobic conditions alone or aerobic conditions alone. It is also preferred that both conditions be combined by changing from the anaerobic to the aerobic or from the aerobic to the anaerobic during the culture.

The thus cultured and harvested cells are disrupted by ordinary means, for example, ultrasonication, enzyme treatment, homogenization, etc., since the bacteria contain NADH oxidase in the cells. Alternatively, the obtained cell-free extract may be subjected to known methods for separation and purification such as salting-out, ion exchange chromatography, gel filtration, etc. (cf., e.g., "METHODS in ENZYMOLOGY", vol. XXII, edited by William B. Jakoby, USA, "Enzyme Purification and Related Techniques", published by Academic Press Inc., pages 333 to 339), whereby NADH oxidase can be isolated.

In the hereinabove, the process for producing NADH oxidase using naturally occurring alkalophilic, facultative anaerobic NADH oxidase-producing bacteria has been described. However, the process of the present invention is not limited to the use of such naturally occurring NADH oxidase-producing bacteria alone. In the present invention, a microorganism transformed with a plasmid by genetic engineering which comprises at least a DNA region containing a gene encoding biosynthesis of NADH oxidase or an NADH oxidase structural gene derived from the NADH oxidase-producing bacteria can also be used. By doing so, the production efficiency of NADH oxidase can further be enhanced.

Hereafter the plasmid used for the transformation of the microorganism and a method for preparing the same are described in more detail.

DESCRIPTION OF THE PREFERRED EMBODIMENTS

The plasmid in accordance with the present invention carries as an essential DNA region at least an enzyme having a function to oxidize NADH with molecular oxygen and regenerate NAD, that is, encode NADH oxidase [DNA region containing a gene encoding biosynthesis of NADH oxidase or an NADH oxidase structural gene] (hereafter sometimes simply referred to as "N region"), is capable of autonomous replication in a host microorganism and is capable of expressing the NADH oxidase structural gene.

The plasmid can also carry a genetic region encoding autonomous replication so as to be able to autonomously replicate in a host microorganism, for example, Escherichia coli. A specific example of such genetic region includes "DNA region containing a gene encoding autonomous replication of Col E1 type plasmid" (hereafter sometimes simply referred to as "S region").

If necessary and desired, the plasmid may also contain a genetic region capable of regulating expression of the NADH oxidase structural gene, for example, in the N region. In such a case, the plasmid can further carry a genetic region capable of regulating expression of the structural gene, specifically, "DNA region of regulatory gene containing a promoter and an operator capable of regulating expression of the NADH oxidase structural gene" (hereafter sometimes simply referred to as "P region").

If necessary and desired, the plasmid may also carry a DNA region encoding other genetic information, for example, a DNA region containing an ampicillin-resistant gene, a DNA region containing a kanamycin-resistant gene or the like which is an antibiotic resistant marker.

Firstly, as the microorganism which is a source for supplying DNA in the N region, any strain is usable so long as it belongs to the alkalophilic, facultative anaerobic bacteria and is capable of producing NADH oxidase. The microorganism may also be variants thereof. A specific example of the strain having these properties which is preferred in the present invention includes strain Ep01 (FERM BP-2744) described above.

DNA in the N region can be prepared by digesting chromosome of the microorganism described above with a suitable restriction endonuclease, for example, Alu I, Hind III, EcoR I, BamH I, etc. As DNA in the N region which is particularly preferably used, there are illustrated a DNA fragment having a size of about 1.6 kb obtained by digesting chromosome of the alkalophilic, facultative anaerobic NADH oxidase-producing bacteria, strain Ep01 (FERM BP-2744) described above with restriction endonucleases Alu I and/or Hind III, a DNA fragment having a size of about 3.6 kb obtained by digesting chromosome of the alkalophilic, facultative anaerobic NADH oxidase-producing bacteria, strain Ep01 with restriction endonucleases EcoR I and BamH I, etc.

Figure 1:
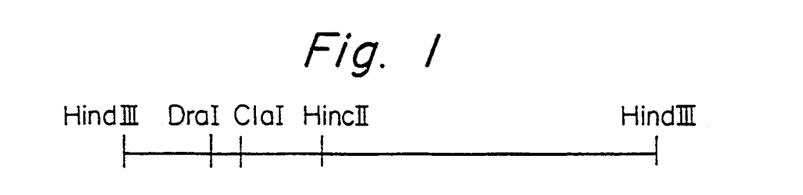
FIG. 1 is a restriction endonuclease map of a DNA fragment having a size of about 1.6 kb containing the NADH oxidase structural gene.
Figure 2:
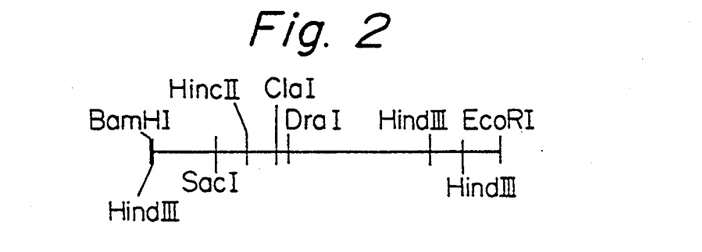
FIG. 2 is a restriction endonuclease map of a DNA fragment having a size of about 3.6 kb containing the gene encoding biosynthesis of NADH oxidase.

The sizes of fragments obtained when the 1.6 kb DNA fragment and the 3.6 kb DNA fragment described above are digested with various restriction endonucleases are shown in Tables 1 and 2. Restriciton endonuclease maps of these DNA fragments are also shown in FIGS. 1 and 2.

In the present invention, the "number of recognition sites" by a restriction endonuclease can be determined from the number of separable fragments which is examined by completely digesting the DNA fragment or plasmid with an excess of a restriction endonuclease and subjeting the digestion product to agarose gel electrophoresis or polyacrylamide gel electrophoresis.

The "size of a fragment" and the sizes of the individual DNA fragments of a plasmid are calculated on the basis of a standard line drawn by migration distances on the same agarose gel of a DNA fragment of a known molecular size obtained by digesting DNA of lambda phage of Escherichia coli with restriction endonuclease Hind III when agarose gel electrophoresis is used; and on the basis of a standard line drawn by migration distances on the same polyacrylamide gel of a DNA fragment of a known molecular size obtained by digesting DNA of 0X174 phage of Escherichia coli with restriction endonuclease Hae III. The size of the plasmid is calculated by adding the sizes of the individual fragments. In the determination of the sizes of the individual DNA fragments, fragments of at least 1 kb is determined by using the results obtained by 1% agarose gel electrophoresis, and fragments of about 0.1 kb to less than 1 kb, by using the results obtained by 4% polyacrylamide gel electrophoresis.

TABLE 1

| (DNA fragment of about 1.6 kb) | | |
|---|---|---|
| Restriction endonuclease | Number of restriction sites | Size (kb) of the fragment |
| Cla I | 1 | 1.2 kb, 0.4 kb |
| Dra I | 1 | 1.3 kb, 0.3 kb |
| Hinc II | 1 | 0.9 kb, 0.7 kb |

TABLE 2

| (DNA fragment of about 3.6 kb) | | |
|---|---|---|
| Restriction endonuclease | Number of restriction sites | Size (kb) of the fragment |
| Cla I | 1 | 2.3 kb, 1.3 kb |
| Dra I | 1 | 2.2 kb, 1.4 kb |
| Hinc II | 1 | 2.6 kb, 1.0 kb |
| Sac I | 1 | 2.9 kb, 0.7 kb |
| Hind III | 3 | 1.6 kb, 0.9 kb, 0.05 kb |

Next, the S region contains a DNA region containing a gene encoding autonomous replication of Col E1 plasmid in which the copy number is 20 to 30 per one chromosome. As a representative example, there is preferably used a DNA fragment of about 4.3 kb obtained by digesting plasmid pBR322 (manufactured by Takara Shuzo Co., Ltd.) with restriction enconucleases EcoR I, Hind III, etc.

Furthermore, as the P region, there is advantageously used a regulatory gene DNA constructed by fusing "−35 region" of trp promoter and "−10 region" of lac UV-5 promoter obtained from, e.g., tryptophan operon and lactose operon, respectively (hereafter simply referred to as Ptac) [cf. deBoer, H. et al., Proc. Natl. Acad. Sci., USA, 80, 21 (1983); Russel, D. R. & Bennet, G. N., Gene, 20, 231 (1982)]. Ptac is repressed by lactose repressor but in lac I° host such as *Escherichia coli* JM109 (manufactured by Takara Shuzo Co., Ltd.), the repression can be released by adding isopropyl-$\beta$-D-thiogalactopyranoside (hereafter merely referred to as IPTG). As Ptac, a DNA fragment containing Ptac derived from plasmid pDR540 (manufactured by Pharmacia Fine Chemicals, Inc.) or isolated Ptac fragment (manufactured by Pharmacia Fine Chemicals, Inc.) can be utilized. In addition, DNA synthesized by a DNA synthesizer (manufactured by Beckman Co., Ltd., System I Plus) which conventionally used to contains optional restriction endonuclease recognition sites at both termini can also be used.

Specific examples of the plasmid having the DNA region as described above include plasmid pNOX1 consisting essentially of three regions of the N region, P region and S region; and plasmid pNOX2 consisting essentially of two regions of the N region and S region. These plasmids pNOX1 and pNOX2 can be prepared, for example, by the process shown below.

As a source for supplying the N region, the culture of the aforesaid alkalophilic, facultative anaerobic NADH oxidase-producing bacteria, strain Ep01 (FERM BP 2744) is used. The strain Ep01 (FERM BP-2744) is cultured under conditions similar to those described above and the cells are collected from the culture. After the cells are disrupted in a conventional manner such as by ultrasonication, homogenization, etc., the chromosomal DNA can be extracted by a known method conventionally used.

The extracted chromosomal DNA is digested with a suitable restriction endonuclease, e.g., Alu I and further with restriction endonuclease Hind III, or directly digested with restriction endonuclease Hind II to give the N region of about 1.6 kb. Further by digestion with, e.g., restriction endonuclease EcoR I and further with restriction endonuclease BamH I, the N region of about 3.6 kb can be obtained.

In the case of constructing plasmid pNOX1, the aforesaid DNA fragment of about 1.6 kb (N region) digested with restriction endonucleases Alu I and/or Hind III is subjected in cloning to a cloning vector such as a plasmid or λ phage, etc. For example, this DNA fragment can be introduced to the Hpa I site of expression cloning vector pPL-Lambda (manufactured by Pharmacia Fine Chemicals, Inc.). In this case, only a fragment digested with restriction endonuclease Alu I can be introduced into the Hpa I site in its original form. Therefore, in the case of digesting with restriction endonuclease Hind III, the fragment can be introduced into the Hpa I site after a linker is ligated thereto or the digested site is rendered the blunt end.

After the DNA fragment-introduced plasmid is transformed to a suitable host *Escherichia coli*, for example, *Escherichia coli* N4830 (manufactured by Pharmacia Fine Chemicals, Inc.) strain, the DNA fragment is expressed by thermal induction at 42° C. for 3 minutes and expression of the desired protein is confirmed by immunoscreening using an NADH oxidase-specific antibody, etc. Thus, the desired clone can easily be obtained. Furthermore, the DNA fragment described above can also be ligated to other expression vector.

As a source for supplying the S region, it is most preferred to use plasmid pBR322 (manufactured by Takara Shuzo Co., Ltd.) described above which is representative of Col E1 plasmid.

As the P region, it is advantageous to use Ptac described above. It is preferred that Ptac be synthesized so as to have optional restriction endonuclease recognition sites at both termini. In this case, it is desired to have the EcoR I cleavage site at the 5' end and the Hind III cleavage site at the 3' end, when pBR322 is used as the vector plasmid.

The Ptac fragment thus prepared is mixed with plasmid pBR322 (S region) digested with restriction endonucleases EcoR I and Hind III and ligated with T4 DNA ligase. Thus, a plasmid in which the Ptac fragment described above is incorporated into plasmid pBR322 can be prepared. Then, the plasmid is cleaved with Hind III and mixed with the DNA fragment containing the NADH oxidase structural gene (N region) which is excised with Alu I and/or Hind III ligated with T4 DNA ligase. By transforming to a suitable host, expression of the NADH oxidase is examined. By doing so, the desired plasmid can be obtained.

The plasmid thus prepared is named plasmid pNOX1 by the present inventors.

Sensitivity of plasmid pNOX1 to restriction endonuclease (number of recognition sites) and size of the digested fragments with the restriction endonuclease are shown in Table 3.

TABLE 3

| Restriction endonuclease | Number of restriction sites | Size (kb) of the fragment |
|---|---|---|
| EcoR I | 1 | 5.9 kb |
| Cla I | 1 | 5.9 kb |

TABLE 3-continued

| Restriction endonuclease | Number of restriction sites | Size (kb) of the fragment |
|---|---|---|
| BamH I | 1 | 5.9 kb |
| Pst I | 1 | 5.9 kb |
| Hind III | 2 | 4.3 kb, 1.6 kb |

In the case of constructing plasmid pNOX2, the aforesaid DNA fragment having a size of about 3.6 kb (N region) is mixed with plasmid pBR322 (S region) digested with restriction endonucleases EcoR I and BamH I and ligated with T4 DNA ligase. Thus, plasmid pNOX2 can be constructed. Then, a suitable host is transformed with the plasmid, the NADH oxidase is expressed thereby to obtain the desired plasmid. The plasmid thus prepared is named pNOX2.

Figure 3:
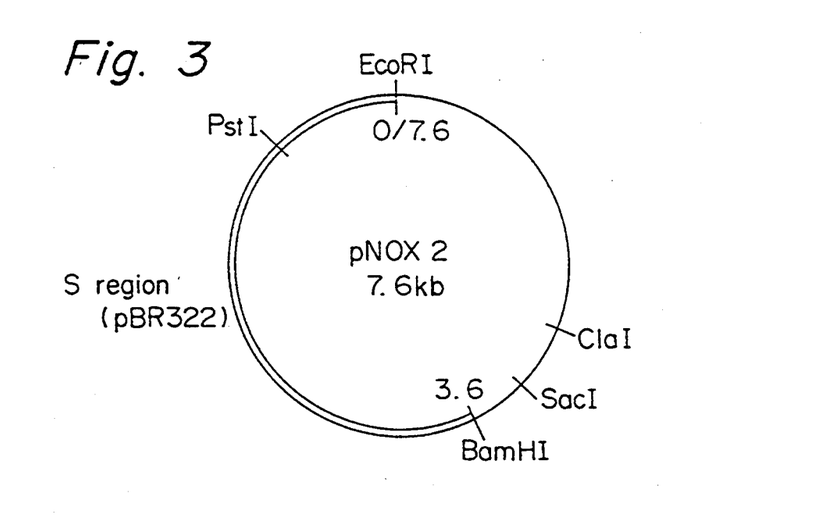
FIG. 3 is a restriction endonuclease map of plasmid pNOX 2.

Sensitivity of plasmid pNOX2 to restriction endonuclease (number of recognition sites) and size (kb) of the digested fragments with the restriction endonuclease are shown in Table 4. In addition, the restriction endonuclease recognition map of this plasmid is shown in FIG. 3.

TABLE 4

| Restriction endonuclease | Number of restriction sites | Size (kb) of the fragment |
|---|---|---|
| EcoR I | 1 | 7.6 kb |
| Cla I | 1 | 7.6 kb |
| BamH I | 1 | 7.6 kb |
| Sac I | 1 | 7.6 kb |
| Pst I | 1 | 7.6 kb |

Next, transformation of a host microorganism with the plasmid thus constructed and a process for producing NADH oxidase using the microorganism are described below.

As a host microorganism which can be utilized for transformation with the plasmid of the present invention, a variety of microorganisms can be used depending upon host-vector system but *Escherichia coli* is particularly preferred. Of *Escherichia coli*, *Escherichia coli* K-12 strain is particularly preferred.

Transformation of the plasmid of the present invention to these host bacteria can be performed in a known conventional manner described in the literature, e.g., M. Mandel, A. Higa; J. Mol. Biol., 53, 159 (1970), etc.

The host bacteria thus transformed can be cultured in a conventional manner thereby to intracellularly produce and accumulate NADH oxidase sufficiently.

The thus cultured and harvested cells are disrupted by ordinary means, for example, ultra-sonication, enzyme treatment, homogenization, etc., since the bacteria contain NADH oxidase in the cells. Alternatively, the obtained cell-free extract may be subjected to known methods for separation and purification such as salting-out, ion exchange chromatography, gel filtration, etc. (cf., e.g., "METHODS in ENZYMOLOGY", vol XXII, edited by William B. Jakoby, USA, "Enzyme Purification and Related Techniques", published by Academic Press Inc., pages 333 to 339), whereby NADH oxidase can be isolated.

The cultivation of the transformed bacteria described above varies depending upon the kind of host bacteria but can be performed generally in synthetic or natural medium conventionally used. Thus, as carbon sources, there may be used various carbohydrates such as glucose, glycerol, fructose, sucrose, molasses, etc. Furthermore, as nitrogen sources, naturally organic nitrogen sources such as tryptone, yeast extract, corn steep liquor, casein hydrolysate, etc. may be used. Most of the naturally organic nitrogen sources can be both nitrogen sources and carbon sources. Further in the case that host bacteria transformed with the plasmid containing the Ptac fragment as the P region, it is preferred that IPTG be added to the medium generally in a concentration of 0.1 mM or more, preferably in a concentration of from about 0.5 mM to about 5 mM during the exponential growth stage after the initiation of culture thereby to induce and express NADH oxidase.

The cultivation can be carried out under aerobic conditions such as shaking culture, aerial spinner deep culture, etc. It is generally desired that the culture temperature be in a range of from about 20° to about 50° C. It is also desired to maintain the pH range of medium during the culture in a neutral to weakly alkaline region. A time period for the culture is generally betwen about 10 hours to about 40 hours.

Enzymological and physicochemical properties of the NADH oxidase produced as described above are shown as follows.

(1) Reaction:

This enzyme oxidizes NADH to form NAD and hydrogen peroxide as shown by the following reaction scheme:

$$NADH + H^+ + O_2 \rightarrow NAD^+ + H_2O_2$$

Figure 4:
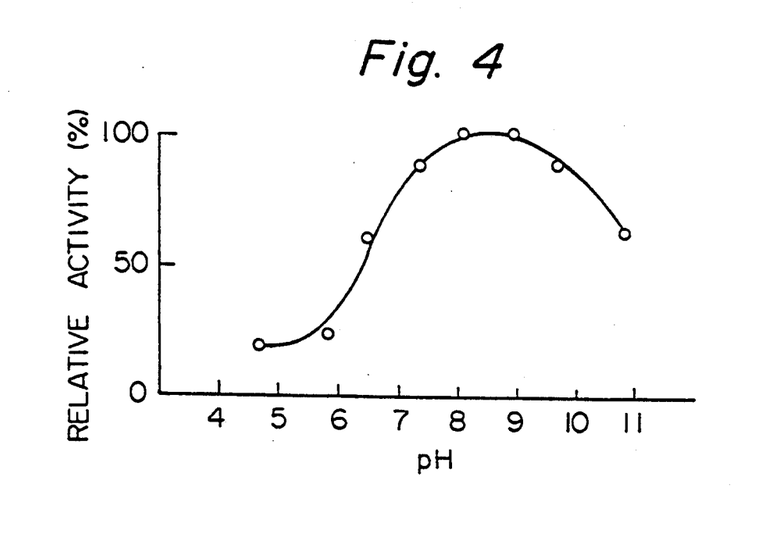
FIG. 4 is a graph showing a relationship between pH and relative activity of the NADH oxidase produced by the process of the present invention.

(2) Optimum pH:

When measured using acetate buffer, Tris buffer and carbonate buffer, this enzyme has the optimum pH at about 8 to about 9 (cf. FIG. 4).

Figure 5:
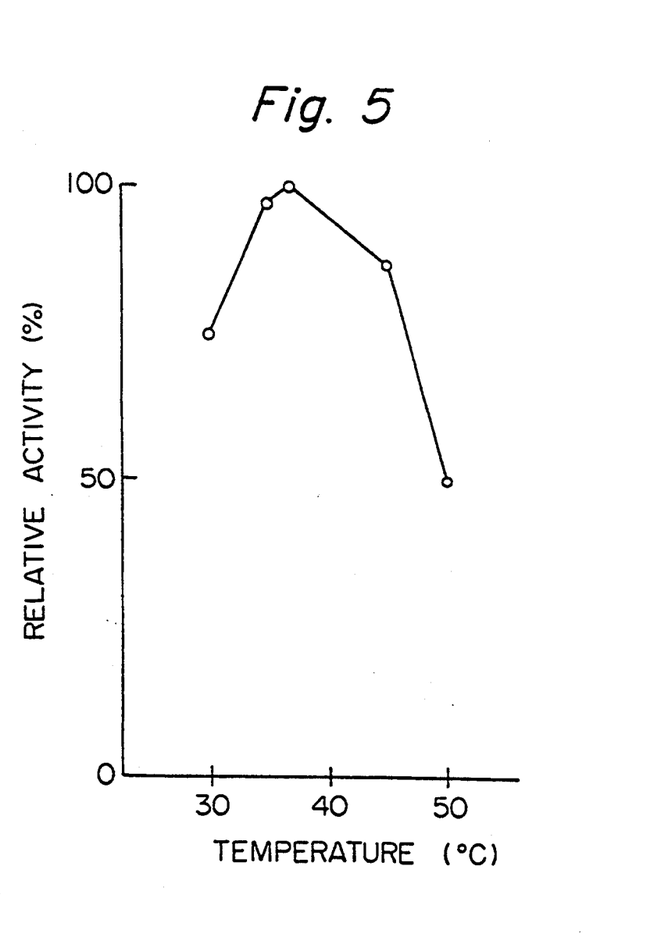
FIG. 5 is a graph showing a relationship between temperature and relative activity of the NADH oxidase produced by the process of the present invention.

(3) Optimum temperature:

When measured using phosphate buffer (pH 7.0), the enzyme has the optimum temperature at about 37° C. (cf. FIG. 5).

(4) Temperature stability:

When the temperature stability of the activity was examined after the enzyme was suspended in the same buffer as used in (3) described above and the suspension was kept at 37° C., the enzyme had the same activity as that of time zero, even 100 hours after. On the other hand, *Leuconostoc mesenteroides* already known maintains its activity at 30° C. even 60 minutes after but reduces the activity to about 60% at 40° C. and to 0% at 50° C., as shown in Journal of Biochemistry, 97, 1285 (1985), FIG. 7B.

(5) Auxotrophy for monovalent cations:

Where NADH oxidase activity of the enzyme solution obtained by dialyzing cell-free bacterial extract against 50 mM Tris buffer is made 100, activities of the enzyme supplemented with $K^+$, $Na^+$ and $NH_4^+$ in a concentration of 20 mM each were 310, 180 and 310, respectively.

(6) NADH oxidase is present in the supernatant fraction obtained after the cell-free extract was subjected to ultracentrifugation at $100,000 \times g$ for an hour.

The qualitative analysis of the enzyme was performed by observing reduction in absorbance of NADH at 340 nm or oxygen consumption in the co-presence of NADH with an oxygen electrode or a manometer. The activity of this enzyme can be determined as follows: that is, to the reaction solution of 1.9 ml of 50 mM buffer and 0.05 ml of the enzyme solution previously kept at a predetermined temperature, is added 0.05 ml of 5 mM NADH to initiate the reaction and decrease of absorbance at 340 nm is then measured. An amount of the enzyme that oxidizes 1 μmol of NADH in one minute is defined to be one unit of the enzyme activity.

The culture of strain Ep01 (FERM BP-2744) or transformants thereof or the NADH oxidase-containing products thereof obtained as described above can be utilized for dehydrogenation of the corresponding substrate by coupling with various dehydrogenase using $NAD^+$ as coenzyme so that it is possible to apply to production of various useful substances and to biochemical reactions.

Examples of dehydrogenases which can be coupled with the NADH oxidase of the NADH oxidase include the following enzymes.

(1) Malate dehydrogenase (EC 1.1.1.38, EC 1.1.1.39) Reaction:

L-malic acid + $NAD^+$ ⇌ pyruvic acid + $CO_2$ + NADH + $H^+$ (2) Alcohol dehydrogenase (EC 1.1.1.1) Reaction:

alcohol + $NAD^+$ ⇌ aldehyde + NADH + $H^+$ (3) Glycerol dehydrogenase (EC 1.1.1.6) Reaction:

glycerol + $NAD^+$ ⇌ dihydroxyacetone + NADH + $H^+$ (4) Lactate dehydrogenase (EC 1.1.1.27) Reaction:

L-lactic acid + $NAD^+$ ⇌ pyruvic acid + NADH + $H^+$ (5) 3-Hydroxybutyrate dehydrogenase (EC 1.1.1.30) Reaction:

D-3-hydroxybutyric acid + $NAD^+$ ⇌ acetoacetic acid + NADH + $H^+$ (6) Isocitrate dehydrogenase (EC 1.1.1.41) Reaction:

isocitric acid + $NAD^+$ ⇌ 2-oxoglutaric acid + $CO_2$ + NADH + $H^+$ (7) Galactose dehydrogenase (EC 1.1.1.48) Reaction:

D-galactofuranose + $NAD^+$ ⇌ D-galactono-γ-lactone + NADH + $H^+$ (8) Testosterone 17β-dehydrogenase (EC 1.1.1.63) Reaction:

testosterone + $NAD^+$ ⇌ 4-androstene-3-dione + NADH + $H^+$ (9) Formaldehyde dehydrogenase (EC 1.2.1.1) Reaction:

formaldehyde + reducing glutathione + $NAD^+$ ⇌ S-formylglutathione + NADH + $H^+$ (10) Formate dehydrogenase (EC 1.2.1.2) Reaction:

formic acid + $NAD^+$ ⇌ $CO_2$ + NADH + $H^+$ (11) Alanine dehydrogenase (EC 1.4.1.1) Reaction:

L-alanine + $H_2$ + $NAD^+$ ⇌ pyruvic acid + $NH_4^+$ + NADH + $H^+$ (12) Glutamate dehydrogenase (EC 1.4.1.2) Reaction:

L-glutamic acid + $H_2$ + $NAD^+$ ⇌ 2-oxoglutaric acid + $NH_4^+$ + NADH + $H^+$

The above examples of the dehydrogenases which can be used for producing useful substances in couple with the NADH oxidase in accordance with the present invention are merely illustratively shown only to assist full understanding of the present invention but the scope of the present invention is not deemed to be limited to these examples.

The dehydrogenation of the substrate in the presence of the NADH oxidase by the dehydrogenase described above proceeds, for example, as follows. Firstly, as a first step of the reaction, the oxidized substrate and NADH are formed. Next, as a second step of the reaction, the formed NADH is converted into $NAD^+$ by the action of the NADH oxidase in the presence of oxygen. The first and second steps are repeated so that a trace amount of $NAD^+$ is recycled, whereby the desired oxidation product of substrate is accumulated.

The above reaction is carried out generally in a buffer. The buffer which can be used is not particularly limited but is desirably a buffer in an alkaline region, preferably a buffer having a pH range of from 8 to 9.5, since the reaction equilibrium of the dehydrogenase reaction is shifted towards the direction of: $NAD^+$ →NADH and by coupling with the NADH oxidase of the present invention having the optimum pH in an alkaline region, dehydrogenation of the substrate readily proceeds. Examples of the buffer in an alkaline region include Tris buffer and carbonate buffer. Amounts of the NADH oxidase of the present invention and the dehydrogenase which are used for the reaction are generally in a range of from 0.05 to 10 units, preferably in a range of from 0.1 to 5 units, respectively. A reaction temperature ranges generally from 20° to 40° C. and a reaction time is generally between about 1 and about 6 hours. The coenzyme can be used generally in a range of from 1 to 200 μM, preferably 5 to 100 μM.

Using the aforesaid malate dehydrogenase as the dehydrogenase capable of being coupled with the NADH oxidase in accordance with the present invention, a process for producing pyruvic acid from L-malic acid is described below in more detail.

In the case that malate dehydrogenase is coupled with the NADH oxidase in accordance with the present invention to produce pyruvic acid from L-malic acid, the reaction proceeds as follows:

In this case, the reaction equilibrium of malate dehydrogenase is shifted to the direction of decreasing NADH in a neutral region so that by the coupling reaction with the NADH oxidase, it is difficult to produce pyruvic acid. However, in an alkaline region, the reaction equilibrium of malate dehydrogenase is shifted to the direction of increasing NADH (NAD+→NADH) so that the coupling reaction with the NADH oxidase in accordance with the present invention proceeds to produce pyruvic acid.

As the buffer used for the reaction Tris buffer, carbonate buffer and the like can be used but Tris buffer is preferred. Tris buffer has suitably a concentration of 1 to 500 mM, preferably 20 to 100 mM, for the reaction. It is preferred that the pH be maintained in a range of from 6 to 10, more preferably in a range of from 7 to 9. For enhancement of the activity of the NADH oxidaes, it is possible to add 0.1 to 50 mM of monovalent cations such as $K^+$, $Na^+$, $NH_4^+$, etc. to the reaction system. It is preferred that these monovalent cations be added in a range of from 1 to 10 mM. Malic acid or malates which are the substrate can be added to the reaction system generally in a concentration of from 10 to 1,000 mM, preferably in a concentration of from 50 to 400 mM. Amounts of the NADH oxidase and the dehydrogenase are generally in a range of from 0.05 to 10 units, preferably in a range of from 0.5 to 5 units, respectively. An amount of $NAD^+$ to be added is generally in a range of from 1 to 200 μM, preferably in a range of from 5 to 100 μM. A reaction temperature ranges generally from 20° to 40° C. and a reaction time is generally between about 1 and about 6 hours. The accumulated pyruvic acid can be recovered in a conventional manner such as crystallization or the like.

Next, the present invention is described in more detail, by referring to the examples below. However, these examples are merely illustratively shown only to assist full understanding of the present invention but the present invention is not deemed to be limited to these examples.

EXAMPLES

Example 1

Production of NADH oxidase using alkalophilic, facultative anaerobic NADH oxidase-producing strain Ep01 (1)

In 900 ml of distilled water were dissolved 1 g of $K_2HPO_4$, 2 g of ammonium nitrate, 200 mg of $MgSO_4.7H_2O$, 5 mg of $FeSO_4.7H_2O$, 700 mg of $CaCl_2.2H_2O$, 3 g of yeast extract, 300 mg of polypeptone, 10 g of xylan and 1 mg of resazurin and, 90 ml each of the solution was dispensed in a serum bottle of a 100 ml volume. After oxygen-free nitrogen gas prepared by boiling, degasifying and passing through a reducing copper column was introduced, each bottle was sealed with a butyl rubber stopper and then with an aluminum cap followed by sterilization at 120° C. for 15 minutes. To this medium was added 10 ml of 10% sodium carbonate aqueous solution (pH 10.6) sterilized at 120° C. for 15 minutes to adjust pH of the medium to 10. Furthermore, titanium (III) citrate solution prepared in a manner similar to the method of A. J. B. Zehnder & K. Wuhrmann et al. described in Science, 194, 1165–1166 was added as a reducing agent in a final concentration of 0.13 mM. Alkalophilic, facultative anaerobic strain Ep01 (FERM BP-2744) was inoculated in the medium and subjected to stationary culture at 40° C. for 20 hours, which was used as a seed culture.

In a serum bottle having a volume of 500 ml each was dispensed 450 ml each of medium having the same composition as described above except for changing 10 g of xylan to 10 g of glucose and, the same procedures were performed. After sterilizing at 120° C. for 15 minutes, 50 ml of 10% sodium carbonate aqueous solution and titanium (III) citrate solution in a final concentration of 0.13 mM were added to the system. The seed culture, 10 ml, described above was inoculated in the medium followed by stationary culture at 40° C. for 24 hours. After completion of the culture, 100 ml of the culture solution was centrifuged at 1,000×g for 20 minutes. After the resulting cells were suspended in 50 mM Tris-hydrochloride buffer, the suspension was centrifuged and the cells were collected to obtain washed cells. After the cells were suspended in 5 ml of the same buffer, the cells were disrupted by ultrasonication and centrifuged. The thus obtained supernatant was a crude enzyme solution. Measurement of NADH oxidase activity of the crude enzyme solution showed 0.25 units/1 ml (one unit indicates an amount of enzyme which oxidizes 1 μmole of NADH).

Example 2

Production of NADH oxidase using alkalophilic, facultative anaerobic NADH oxidase-producing strain Ep01 (2)

In an Erlenmeyer flask having a volume of 500 ml each was dispensed 90 ml each of medium having the same composition described in Example 1 except for using 10 g of glucose instead of 10 g of xylan and containing no resazurin. After sterilizing at 120° C. for 15 minutes, 10% sodium carbonate aqueous solution which had been separately sterilized by heating was added thereto to adjust the pH to 10. Thereafter, 5 ml of the seed culture described in Example 1 was inoculated on the medium followed by shaking culture at 30° C. for 20 hours. After completion of the culture, 100 ml of the culture solution was centrifuged and the resulting cells were suspended in 5 ml of 50 mM Tris-hydrochloride buffer. The cells were disrupted by ultrasonication and centrifuged. The thus obtained supernatant was a crude enzyme solution. The activity was 0.18 units/ml.

Example 3

Construction of plasmid pNOX1 and transformation of Escherichia coli using the plasmid (A) Preparation of chromosomal DNA of alkalophilic, facultative anaerobic NADH oxidase-producing strain Ep01:

In 900 ml of distilled water were dissolved 1 g of $K_2HPO_4$, 2 g of ammonium nitrate, 200 mg of $MgSO_4.7H_2O$, 5 mg of $FeSo_4.7H_2O$, 700 mg of $CaCl_2.2H_2O$, 3 g of yeast extract, 300 mg of polypeptone, 10 g of xylan and 1 mg of resazurin and, 90 ml each of the solution was dispensed in a serum bottle of a 100 ml volume. After oxygen-free nitrogen gas prepared by boiling, degasifying and passing through a reducing copper column was introduced, each bottle was sealed with a butyl rubber stopper and then with an aluminum cap followed by sterilization at 120° C. for 15 minutes. To this medium was added 10 ml of 10% sodium carbonate aqueous solution (pH 10.6) sterilized at 120° C. for 15 minutes to adjust pH of the medium to 10. Furthermore, titanium (III) citrate solution prepared in a manner similar to the method of A. J. B. Zehnder & K. Wuhrmann et al. described in Science, 194, 1165–1166 was added as a reducing agent in a final concentration of 0.13 mM. Alkalophilic, facultative anaerobic strain Ep01 (FERM BP-2744) was inoculated in the medium and subjected to stationary culture at 40° C. for 20 hours, which was used as a seed culture.

In a serum bottle having a volume of 500 ml each was disensed 450 ml each of medium having the same composition as described above except for changing 10 g of xylan to 10 g of glucose and, the same procedures were performed. After sterilizing at 120° C. for 15 minutes, 50 ml of 10% sodium carbonate aqueous solution and titanium (III) citrate solution in a final concentration of 0.13 mM were added to the system. The seed culture, 10 ml, described above was inoculated in the medium followed by stationary culture at 40° C. for 24 hours. After completion of the culture, 100 ml of the culture solution was centrifuged at 1,000×g for 20 minutes. After the resulting cells were suspended in 50 mM Tris-hydrochloride buffer (pH 8.0)–50 ml of 10 mM EDTA.2Na solution. Next, lysozyme was added to the system in a final concentration of 2 mg/ml. After the mixture was settled for 5 minutes, 6 ml of 10% sodium dodecylsulfate solution was added thereto followed by keeping at 65° C. for 30 minutes. To the lysate solution was added 15 ml of 5M NaCl solution and the mixture was cooled at 0° C. for an hour. The whole amount was centrifuged (12,000×g, 60 minutes, 4° C.) the supernatant fraction was fractionated, and 2-fold amount of ethanol was added to the fraction. After mixing, centrifugration (5,000×g, 10 minutes, 4° C.) was performed. The resulting precipitates were dissolved in 10 mM Tris buffer (pH 7.5) and 1 mM EDTA.2Na solution. The solution was treated with phenol (treatment for removing protein) and treated with RNase to give DNA.

(B) Preparation of DNA fragment containing NADH oxidase structural gene (N region):

The chromosomal DNA, 50 μg, prepared in (A) described above was reacted with 100 units of restriction endonuclease Alu I at 30° C. for an hour to give a solution of the Alu I digestion product of the chromosomal DNA. The solution of the Alu I digestion product was subjected to agarose gel electrophoresis and the gel was fractionated to obtain a DNA fragment having a size of 1 to 4 kb. The gel was purified in a conventional manner by dissolving in NaI and adsorbing the DNA fragment onto glass powders [B. Vogelstein & D. Gillespie, Proc. Natl. Adad. Sci. USA, 76, 615–619 (1979)].

One μg of plasmid pPL-Lambda (manufactured by Pharmacia Fine Chemicals, Inc.) was digested with a restriction endonuclease Hpa I at 30° C. for an hour. The thus obtained solutions of the digestion products were mixed with the Alu I digestion product and 50 mM Tris buffer (pH 7.6), 10 mM dithiothreitol, 1 mM ATP, 10 mM MgCl₂ and 1 unit of T4 ligase (the concentration of each component was shown by the final concentration) were added to the mixture. The reaction was carried out at 16° C. for 15 hours to ligate them.

Using this solution, *Escherichia coli* N4830 strain (manufactured by Pharmacia Fine Chemicals, Inc.) was transformed in a conventional manner [cf., N. Mandel, A. Higa, J. Mol. Biol., 53, 159 (1970)] and the transformants were plated on medium obtained by adding ampicillin to L medium (10 g of tryptone, 5 g of yeast extract, 5 g of NaCl, 1 g of glucose and 1 liter of distilled water, pH 7.2) in a concentration of 50 μg/ml and solidifying with 1.5% agar (hereinafter referred to as LA medium) followed by culturing at 30° C. for 20 hours to form colonies. A nitrocellulose membrane was put on the medium and thermal induction was performed at 42° C. for 3 hours. The colonies on the membrane filter were lyzed. After blocking the non-specific binding to the membrane with bovine serum albumin, the membrane was treated with anti-NADH oxidase antibody prepared by immunizing a rabbit with the purified NADH oxidase immunoscreening was performed. After the membrane was further treated with horse-radish peroxidase-bound anti-rabbit IgG, a color was formed in the system of hydrogen peroxide-3,3-diaminobenzidine or in the system of hydrogen peroxide-4-chloro-1-naphthol to select the desired colony. The transformants were obtained in a yield of $5 \times 10^{-5}$.

The thus obtained 5 clones were cultured in LA liquid medium at 30° C. for 20 hours. Then, after thermal induction at 42° C. for 3 hours, the cells were collected by centrifugation (12,000 rpm, 20 minutes). After 1 g of the cells was suspended in 2 ml of Tris buffer (pH 7.8), the suspension was ultrasonicated and centrifuged to remove the residue. With respect to the resulting cell-free extract, a strain showing the largest oxygen absorption upon oxidation of NADH was selected using an oxygen electrode (manufactured by Yellow Springs Instrument Co.). From this strain, a plasmid was extracted by the alkaline-SDS method [cf., T. Maniatis, E. F. Fritsch, H. Sambrook, "Molecular Cloning", 90–91 (1982)]. The plasmid was digested with restriction endonuclease EcoR I and its molecular weight was examined by agarose gel electrophoresis. It was revealed that the DNA fragment of about 2.0 kb was inserted into pPL-lambda.

Since Hpa I recognition site used for the insertion into pPL-lambda could not be used by ligation between the blunt ends, other recognition site with restriction endonuclease was surveyed. As the result, it was revealed that the inserted DNA fragment could be excised as a fragment of about 1.6 kb by digestion with Hind III. The Hind III-digestion product of the extracted plasmid was isolated by agarose gel electrophoresis and the DNA fragment of 1.6 kb was prepared from the gel by the aforesaid NaI-glass powder method.

(C) Synthesis of Ptac

Promoter Ptac having the DNA sequence as shown below was synthesized by a DNA synthesizer (System-1 Plus manufactured by Beckmann Co.).

```
AATTCTGTTGACAATTAATCATCGGCTCGTATAATG
    GACAACTGTTAATTAGTAGCCGAGCATATTAC
TGYGGAATTGTGAGCGGATAACAATTTCACACAGGAA
ACACCTTAACACTCGCCTATTGTTAAAGTGTGTCCTT
ACA
TGTTCGA
```

(D) Construction of plasmid pNOX1 and transformation of *Escherichia coli* using the plasmid With the digestion product solution obtained by digesting 1 μg of plasmid pBR322 with restriction endonucleases nucleases EcoR I and Hind III (1 unit each) at 30° C. for an hour were mixed 1 μg of the DNA fragment of 1.6 kb prepared in (B) described above and 0.1 μg of the Ptac DNA fragment prepared in (C) described above. Tris buffer (pH 7.6), dithiothreitol, ATP, MgCl₂ and T4 ligase were added to the mixture in final concentrations of 50 mM, 10 mM, 1 mM, 1 mM, 10 mM and 1 unit, respectively. The reaction was carried out at 16° C. for 15 hours to ligate them. Using this solution, *Escherichia coli* K-12 type strain JM109 (manufactured by Takara Shuzo Co., Ltd.) was transformed in a conventional manner and the transformants were plated on LA medium followed by culturing at 37° C. for 24 hours, From the grown strain, plasmids were extracted by the alkaline-SDS method. The plasmids were digested with restriction endonucleaes EcoR I (5 units) and Cla I (5 units). Measurement of its molecular weight by agarose gel electrophoresis showed that each one plasmid in which NADH oxidase structural gene-containing DNA fragment (1.6 kb) was bound to the Hind III digestion site in a different configuration was present. Of the plasmids, the plasmid forming a fragment of about 1.2 kb in size by EcoR I and Cla I digestion was named pNOX1. *Escherichia coli* K-12 type strain JM109 transformed with this plasmid pNOX1 was named NY01. The NY01 strain has been deposited in the Fermentation Research Institute, Agency of Industrial Science and Technology, 1-3, Higashi 1-chome, Tsukubashi, Ibaraki-ken 305, Japan under the deposit number, FERM P-10542 on Feb. 16, 1989 [transferred to international deposit (FERM BP-2745) on Jan. 29, 1990 under the Budapest Treaty].

Example 4

Construction of plasmid pNOX2 and transformation of *Escherichia coli* using the plasmid (A) Preparation of DNA fragment for encoding biosynthesis of NADH oxidase (N region):

The chromosomal DNA, 50 µg, prepared in Example 3, (A) was digested with 100 units each of restriction endonucleases EcoR I and BamH I at 30° C. for an hour to give a solution of the EcoR I and BamH I digestion product of the chromosomal DNA. The solution of the digestion product described above was subjected to agarose gel portion electrophoresis to excise a gel containing DNA fragment having a size of 1 to 4 kb. The gel was dissolved in a conventional manner in NaI and adsorbing the 3.6 Kb DNA fragment onto glass powders [B. Vogelstein & D. Gillespie, Proc. Natl. Adad. Sci. USA, 76, 615–619 (1979)].

(B) Construction of plasmid pNOX2 and transformation of *Escherichia coli* using the plasmid One microgram of plasmid pBR322 was reacted with restriction endonucleases EcoR I and BamH I (1 unit each) at 30° C. for an hour to digest. With the thus obtained digestion product solution was mixed 1 µg of the DNA fragment of 3.6 kb (N region) prepared in (A) described above. This buffer (pH 7.6), dithiothreitol, ATP, MgCl$_2$ and T4 ligase were added to the mixture in final concentrations of 50 mM, 10 mM, 1 mM, 1 mM, 10 mM and 1 unit, respectively. The reaction was carried out at 16° C. for 15 hours to ligate them.

Using this solution, *Escherichia coli* HB101 strain (manufactured by Takara Shuzo Co., Ltd.) was transformed in a conventional manner [cf., M. Mandel, A. Higa, J. Mol. Biol., 53, 159 (1970)] and the transformants were plated on medium obtained by adding ampicillin to L medium (10 g of tryprone, 5 g of yeast extract, 5 g of NaCl, 1 g of glucose and 1 liter of distilled water, pH 7.2) in a concentration of 50 µg/ml and solidifying with 1.5% agar followed by culturing at 30° C. for 20 hours to form colonies. A nitrocellulose membrane was put on the medium and thermal induction was performed at 42° C. for 3 hours. The colonies on the membrane filter were lyzed. After blocking the non-specific binding to the membrane with bovine serum albumin, the membrane was treated with anti-NADH oxidase prepared by immunizing a rabbit with the purified NADH oxidase, immunoscreening was performed. After the membrane was further treated with horse-radish peroxidase-bound anti-rabbit IgG, a color was formed in the system of hydrogen peroxide-3,3-diaminobenzidine or in the system of hydrogen peroxide-4-chloro-1-naphthol to select the desired colony. The transformants were obtained in a yield of $5 \times 10^{-5}$.

The thus obtained 5 clones were cultured in L medium at 30° C. for 20 hours and the cells were collected by centrifugation (12,000 rpm, 20 minutes). After 1 g of the cells was suspended in 2 ml of Tris buffer (pH 7.8), the suspension was ultrasonicated and centrifuged to remove the residue. With respect to the resulting cell-free extract, a strain showing the largest oxygen absorption upon oxidation of NADH was selected using an oxygen electrode (manufactured by Yellow Springs Instrument Co.). From this strain, a plasmid was extracted by the alkaline-SDS method [cf., T. Maniatis, E. F. Fritsch, H. sambrook, "Molecular Cloning", 90–91 (1982)]. The plasmid was digested with restriction endonucleases EcoR I and BamH I. Examination of its molecular weight by agarose gel electrophoresis revealed that the DNA fragment of 3.6 kb was inserted into pBR322 at the digestion sites with EcoR I and BamH I. This plasmid was named pNOX2. *Escherichia coli* K-12 type strain HB101 (manufactured by Takara Shuzo Co., Ltd.) transformed with this plasmid pNOX2 was named NY02. The NY02 strain has been deposited in the Fermentation Research Institute, Agency of Industrial Science and Technology, 1-3, Higashi 1-chome, Tsukubashi, Ibaraki-ken 305, Japan under the deposit number, FERM P-10943 on Aug. 10, 1989 [transferred to international deposit (FERM BP-2746) on Jan. 29, 1990 under the Budapest Treaty].

Example 5

Production of NADH oxidase using *Escherichia coli* K-12 type strains (NY01 and NY02)

In an Erlenmeyer flask having a 500 ml volume was separately charged 100 ml of M9S medium (5.8 g of Na$_2$HPO$_4$, 3 g of KH$_2$PO$_4$, 5 g of NaCl, 1 g of NH$_4$Cl, 1 liter of distilled water, 0.5% of glycerol, 0.5% of Casamino acids and 4 µg/ml thiamine hydrochloride) followed by sterilization at 120° C. for 15 minutes. Ampicillin was added to the medium in a concentration of 40 µg/ml. NY01 strain obtained in Example 3 and its parent JM109 strain, and NY02 strain obtained in Example 4 and its parent HB101 strain were independently inoculated in the medium, respectively, followed by culturing at 30° C. for about 16 hours. The culture was inoculated in 100 ml of fresh medium in a dilution rate of 1:100. The culture was continued at 30° C. In the case of NY01 strain, IPTG was added thereto in a final concentration of 2 mM at the stage when absorbance at 650 nm reached about 1.0, thereby to release inhibition of Ptac with lactose repressor and the culture was further continued. About 4 hours after, the cells were collected by centrifugation (12,000 rpm, 20 minutes). The collected cells were suspended in 1 ml of Tris buffer and the suspension was ultrasoncated. The residue was removed by centrifugation (12,000 rpm, 20 minutes). Furthermore ultracentrifugation was performed at 100,000×g for an ahour to minimize the influence of NADH dehydrogenase of *Escherichia coli* present in the membrane fraction. The supernatant was made as an enzyme solution.

The activity of NADH oxidase was determined as follows. That is, to the reaction solution of 1.9 ml of 50 mM potassium phosphate buffer and 0.05 ml of the enzyme solution described above previously kept at a predetermined temperature, 0.05 ml of 5 mM NADH was added to initiate the reaction and decrease of absorbance at 340 nm was then measured. An amount of the enzyme that oxidizes 1 μmol of NADH for one minute is defined to be one unit of the enzyme activity.

With the thus obtained enzyme solution, the activity was measured at 37° C. The results are shown in Table 5 described below. For comparison, the activity of an enzyme solution prepared by culturing alkalophilic, facultative anaerobic bacteria Ep01 (FERM BP-2744) which is a source for supplying NADH oxidase gene by the procedures described in Example 1 is also shown in Table 5.

TABLE 5

| Strain | Specific activity of NADH oxidase |
|---|---|
| Ep01 (FERM BP-2744) | 0.05 unit/mg protein |
| JM109 | 0.02 unit/mg protein |
| NY01 (FERM BP-2745) | 0.2 unit/mg protein |
| HB101 | 0.01 unit/mg protein |
| NY02 (FERM BP-2746) | 1.2 unit/mg protein |

As shown in Table 5, when the strains (NY01 and NY02) transformed with the plasmids of the present invention were used, the specific activity of NADH oxidase was enhanced to more than 4 times and 20 times, respectively, as compared to the parent strain (Ep01) which is the source of the gene. At the same time, it was revealed that the plasmids of the present invention could express NADH oxidase efficiently in Escherichia coli K-12 type strains.

Example 6

Production of pyruvic acid

Using the NADH oxidase enzyme solution (supernatant obtained by ultracentrifugation at 100,000×g for an hour) obtained in Example 5, coupling reaction was performed with malate dehydrogenase [purified by the method of Tokushige et al. (J. Biochem., 73, 169–180, 1973) from Escherichia coli K-12 ATCC 27325] and pyruvic acid was produced using L-malic acid as substrate.

The NADH oxidase enzyme solution described above was added to a reaction solution [containing 200 mM L-malic acid, 1 mM manganese chloride, 50 μM NAD+, 2.5 units/ml malate dehydrogenase and 50 mM Tris buffer (pH 8.5)] so that its protein concentration was 2 mg/ml. The reaction was carried out at 37° C. for 4 hours. After the reaction, amounts of pyruvic acid and succinic acid were quantitatively determined by high performance liquid chromatography. The results are shown in Table 6.

For comparison, amounts of pyruvic acid and succinic acid produced when NADH oxidase obtained from Brevibacterium flavum MJ233 (FERM BP-1497), Leuconostoc mesenteroides (ATCC 8042) and Ep01 strain (FERM BP-2744) was used for the recyckle of the NAD+ were also quantitatively determined. However, in the case of Brevibacterium flavum MJ233, the NADH oxidase activity was found in the precipitate portion obtained after ultracentrifugation at 100,000×g for an hour and this precipitate fragment was used as the enzyme solution.

TABLE 6

| Strain | Amount of pyruvic acid produced (mM) | Amount of succinic acid produced (mM) |
|---|---|---|
| Brevibacterium flavum MJ233 (FERM BP-1497) | 20 | 28 |
| Leuconostoc mesenteroides (ATCC 8042) | 2 | 0 |
| Ep01 (FERM BP-2744) | 14 | 0 |
| NY01 (FERM BP-2745) | 28 | 0 |
| NY02 (FERM BP-2746) | 98 | 0 |

As shown in Table 6, when the NADH oxidases derived from NY01 and NY02 strains of the present invention were used, pyruvic acid could be efficiently produced from L-malic acid in high yields, without by-producing succinic acid.

While the invention has been described in detail and with reference to specific embodiments thereof, it is apparent to one skilled in the art that various changes and modifications can be made therein without departing from the spirit and the scope of the present invention.

What we claim is:

1. A process for producing NADH oxidase, which comprises culturing an Escherichia coli K-12 type strain transformed with a recombinant plasmid comprising:

(a) a DNA fragment containing an NADH oxidase structural gene isolated from an alkalophilic, facultative anaerobic NADH oxidase-producing bacterium, strain Ep01, FERM BP-2744, having an optimum growth pH in an alkaline region;

(b) a DNA fragment having a promotor and an operator which function for the expression of said NADH oxidase structural gene; and (c) a DNA fragment containing autonomous replication genes obtained from Col E1 type plasmid, and recovering from the cultured cells NADH oxidase having the following enzymological properties:

(1) Reaction
       Oxidizes NADH to form NAD+ and hydrogen peroxide as shown by the following reaction scheme:

$NADH + H^+ + O_2 \rightarrow NAD^+ + H_2O_2$;

(2) Optimum pH
       pH 8–9;
    (3) Optimum temperature
       About 37° C. when measured using phosphate buffer (pH 7.0);
    (4) Temperature stability
       No activity reduction is observed when kept in a phosphate buffer, pH 7.0 at 37° C. for 100 hours;
    (5) Auxotrophy for monovalent cations
       Activated with monovalent cations;
    (6) Present in the supernatant fraction obtained after the cell-free extract is subjected to ultracentrifugation at 100,000×g for an hour; and
    (7) No production of succinic acid occurs from L-malic acid when used in a coupling reaction with malate dehydrogenase.

2. The process of claim 1, wherein said Escherichia coli K-type strain is an Escherichia coli NY01, FERM BP-2745.

3. The process of claim 1, wherein said DNA fragment (a) of said recombinant plasmid is a DNA fragment having a size of about 1.6 kb.

4. The process of claim 1, wherein said DNA fragment (b) of said recombinant plasmid is a DNA fragment constructed by fusing the "−35 region" of trp promoter and "−10 region" of lac UV-5 promoter.

5. The process of claim 1, wherein said DNA fragment (c) of said recombinant plasmid is a DNA fragment obtained from plasmid pBR322.

6. The process of claim 1, wherein said recombinant plasmid is a plasmid which comprises:
 (a) a DNA fragment having a size of about 1.6 kb isolated from an alkalophilic, facultative anaerobic NADH oxidase-producing bacterium, strain Ep01, FERM BP-2744, having an optimum growth pH in an alkaline region;
 (b) a DNA fragment constructed by fusing the "−35 region" of trp promotor and "−10 region" of lac UV-5 promotor; and
 (c) a DNA fragment obtained from plasmid pBR322.

7. The process of claim 6, wherein said recombinant plasmid is a plasmid pNOX1.

8. A process for producing NADH oxidase, which comprises culturing an *Escherichia coli* K-12 type strain transformed with a recombinant plasmid comprising:
 (a) a DNA fragment containing a gene encoding biosynthesis of NADH oxidase isolated from an alkalophilic, facultative anaerobic NADH oxidase-producing bacterium, strain Ep01, FERM BP-2744, having an optimum growth pH in an alkaline region; and
 (b) a DNA fragment containing autonomous replication genes obtained from Col E1 type plasmid, and recovering from the culture NADH oxidase having the following enzymological properties:
 (1) Reaction
  Oxidizes NADH to form NAD+ and hydrogen peroxide as shown by the following reaction scheme:

$NADH + H^+ + O_2 \rightarrow NAD^+ + H_2O_2$;

(2) Optimum pH
  pH 8–9;
 (3) Optimum temperature
  About 37° C. when measured using phosphate buffer (pH 7.0);
 (4) Temperature stability
  No activity reduction is observed when kept in a phosphate buffer, pH 7.0 at 37° C. for 100 hours;
 (5) Auxotrophy for monovalent cations
  Activated with monovalent cations;
 (6) Present in the supernatant fraction obtained after the cell-free extract is subjected to ultracentrifugation at 100,000×g for an hour; and
 (7) No production of succinic acid occurs from L-malic acid when used in a coupling reaction with malate dehydrogenase.

9. The process of claim 8, wherein said *Escherichia coli* K-type strain is an *Escherichia coli* NY02, FERM BP-2746.

10. The process of claim 8, wherein said DNA fragment (a) of said recombinant plasmid is a DNA fragment having a size of about 3.6 kb.

11. The process of claim 8, wherein said DNA fragment (b) of said recombinant plasmid is a DNA fragment obtained from plasmid pBR322.

12. The process of claim 8, said recombinant plasmid is a plasmid which comprises:
 (a) a DNA fragment having a size of about 3.6 kb derived from an alkalophilic, facultative anaerobic NADH oxidase-producing bacterium, strain Ep01, FERM BP-2744, having an optimum growth pH in an alkaline region, and
 (b) a DNA fragment obtained from plasmid pBR322.

13. The process of claim 12, wherein said recombinant plasmid is a plasmid pNOX2.

14. A recombinant plasmid which comprises:
 (a) a DNA fragment containing an NADH oxidase structural gene isolated from an alkalophilic, facultative anaerobic NADH oxidase-producing bacterium, strain Ep01, FERM BP-2744, having an optimum growth pH in an alkaline region;
 (b) a DNA fragment having a promotor and an operator which function for the expression of said NADH oxidase structural gene; and
 (c) a DNA fragment containing autonomous replication genes obtained from Col E1 type plasmid.

15. The plasmid according to claim 14 wherein said DNA fragment (a) containing NADH oxidase structural gene is a DNA fragment having a size of about 1.6 kb.

16. The recombinant plasmid according to claim 14 wherein said DNA fragment (b) is a DNA fragment constructed by fusing the "−35 region" of trp promotor and "−10 region" of lac UV-5 promotor.

17. The recombinant plasmid according to claim 14 wherein said DNA fragment (c) is a DNA fragment obtained from plasmid pBR322.

18. An *Escherichia coli* K-12 type strain which is transformed with the plasmid of claim 14.

19. A recombinant plasmid which comprises:
 (a) a DNA fragment having a size of about 1.6 kb isolated from an alkalophilic, facultative anaerobic NADH oxidase-producing bacterium, strain Ep01, FERM BP-2744, having an optimum growth pH in an alkaline region;
 (b) a DNA fragment constructed by fusing the "−35 region" of trp promotor and "−10 region" of lac UV-5 promotor; and
 (c) a DNA fragment obtained from plasmid pBR322.

20. The recombinant plasmid according to claim 19 which is a plasmid pNOX1.

21. A recombinant plasmid which comprises:
 (a) a DNA fragment containing a gene encoding biosynthesis of NADH oxidase isolated from an alkalophilic, facultative anaerobic NADH oxidase-producing bacterium, strain Ep01, FERM BP-2744, having an optimum growth pH in an alkaline region; and
 (b) a DNA fragment containing autonomous replication genes obtained from Col E1 type plasmid.

22. The recombinant plasmid according to claim 21 wherein said DNA fragment (a) is a DNA fragment having a size of about 3.6 kb.

23. The recombinant plasmid according to claim 21 wherein said DNA fragment (b) is a DNA fragment obtained from plasmid pBR322.

24. An *Escherichia coli* K-12 type strain which is transformed with the plasmid of claim 21.

25. A recombinant plasmid which comprises:

(a) a DNA fragment having a size of about 3.6 kb derived from an alkalophilic, facultative anaerobic NADH oxidase-producing bacterium, strain Ep01, FERM BP-2744, having an optimum growth pH in an alkaline region; and (b) a DNA fragment obtained from plasmid pBR322.

26. The recombinant plasmid according to claim 25 which is a plasmid pNOX2.

27. An *Escherichia coli* K-12 type strain which is transformed with the plasmid pNOX1.

28. An *Escherichia coli* K-12 type strain which is transformed with the plasmid pNOX2.

29. An *Escherichia coli* NY01, FERM BP-2745.

30. An *Escherichia coli* NY02, FERM BP-2746.

* * * * *